United States Patent
Harris

(10) Patent No.: US 11,437,137 B1
(45) Date of Patent: Sep. 6, 2022

(54) METHOD, APPARATUS, AND COMPUTER PROGRAM PRODUCT FOR USING MACHINE LEARNING TO ENCODE A HEALTHCARE CLAIM AS A PREDEFINED SIZED VECTOR

(71) Applicant: Change Healthcare Holdings, LLC, Nashville, TN (US)

(72) Inventor: Benjamin Harris, San Francisco, CA (US)

(73) Assignee: CHANGE HEALTHCARE HOLDINGS, LLC, Nashville, TN (US)

( * ) Notice: Subject to any disclaimer, the term of this patent is extended or adjusted under 35 U.S.C. 154(b) by 496 days.

(21) Appl. No.: 16/515,757

(22) Filed: Jul. 18, 2019

(51) Int. Cl.
*G06F 16/22* (2019.01)
*G16H 40/00* (2018.01)
*G06Q 40/08* (2012.01)
*G06Q 30/04* (2012.01)
*G16H 10/60* (2018.01)

(52) U.S. Cl.
CPC ............ *G16H 40/00* (2018.01); *G06F 16/22* (2019.01); *G06F 16/2237* (2019.01); *G06Q 30/04* (2013.01); *G06Q 40/08* (2013.01); *G16H 10/60* (2018.01)

(58) Field of Classification Search
None
See application file for complete search history.

(56) References Cited

U.S. PATENT DOCUMENTS 10,891,352 B1 * 1/2021 Hane ................. G06F 40/242

OTHER PUBLICATIONS

Mullenbach et al., Explainable Prediction of Medical Codes from Clinical Text, 2018 (Year: 2018).*
Choi, E. et al. "Multi-layer Representation Learning for Medical Concepts" [online] [retrieved Sep. 6, 2019], retrieved from the Internet, URL:<https://arxiv.org/pdf/1602.05568.pdf> dated Feb. 17, 2016.
Loew, Let al. "A Self-Attention Network for Hierarchical Data Structures with an Application to Claims Management" [online] [retrieved May 28, 2019], retrieved from the Internet, <https://arxiv.org/pd//1808.10543.pdf> dated Aug. 30, 2018.

* cited by examiner

*Primary Examiner* — Dawaune A Conyers
(74) *Attorney, Agent, or Firm* — Myers Bigel, P.A.

(57) ABSTRACT

A method, apparatus and computer program product are provided for generating a predefined sized vector representative of a healthcare claim including a variable number of service lines. A neural network is trained to identify hierarchical relationships between claim lines and services lines and to represent the relationships in the predefined sized vector. The predefined sized vector may be used to make predictions regarding adjudication, such as probability of denial (claim-level or service-level), days to pay, probability of being paid as a diagnosis related group (DRG), allowed amount, and/or denial reason. Predictions may also be made from the predefined sized vector relating to the likelihood and/or identification of missing procedure codes.

16 Claims, 4 Drawing Sheets

METHOD, APPARATUS, AND COMPUTER PROGRAM PRODUCT FOR USING MACHINE LEARNING TO ENCODE A HEALTHCARE CLAIM AS A PREDEFINED SIZED VECTOR

TECHNOLOGICAL FIELD

Embodiments of the present invention relate generally to healthcare transactions and, more particularly, to methods, apparatuses, and computer program products for using machine learning to encode a healthcare claim.

BACKGROUND

In the healthcare insurance industry, healthcare providers, billers, and medical coders face an increasingly complex system of claims processing methodologies and adjudication processes. Different payors may have different requirements for what data needs to be present in a claim for a claim to be paid, and the requirements may change over time. Similarly, as medical practices evolve, new services and/or diagnoses may be included in insurance claims, such that medical coders need to understand the changes in order to code a claim that will likely be paid.

Claim records often reflect claim-level information regarding the overall claim, any number of diagnoses, and information regarding services provided during a patient visit. Depending on how all this information is coded within a claim, a claim could be denied for payment such that the claim needs to be corrected, or modified by the biller or medical coder to include additional information.

Claims reflecting particularly complex patient visits may include hundreds of services lines, each associated with a service rendered during a patient visit. For example, a hospital visit spanning several days may be submitted as a single claim representative of the hospital visit, but may further include or be associated with hundreds of service lines. A service line may reflect a service or interval of service, such that a separate service line is included in the claim for every 15 minutes of an intravenous (IV) therapy or drip, for example. In this regard, any number of service lines, from zero to hundreds or more could be present in a single claim, each representing different intervals of the same or similar IV therapy. As another example, a service line may reflect a more significant procedure such as a surgery. The different service lines may therefore have varying levels of significance within the overall claim. The service lines may relate to the overall claim-level record in different ways, and may further relate to other service lines within the claim. The relations amongst the various claim record components can impact how the claim is processed and adjudicated.

Machine learning algorithms may be used to process claims and attempt to make predictions regarding the claim. However, many machine learning models may require a fixed size input for solving problems, which presents a challenge in utilizing such algorithms on variable-length claims (such as claims having an unpredictable number of service lines).

BRIEF SUMMARY

Methods, apparatuses, and computer program products are therefore provided for using machine learning to encode a healthcare claim as a predefined sized vector. Encoding healthcare claims as a predefined sized vector enables a neural network to identify patterns and make predictions regarding the healthcare claims, such as predictions regarding adjudication, and/or other information expected in the healthcare claim. The predictions may be provided to the biller or other user in real-time or near real-time as the claim details are provided and/or coded. Example embodiments therefore provide feedback to the user, prior to claim processing and/or adjudication, that may assist the user in modifying the claim to improve the chances of payment, correct any potential discrepancies, enter services or diagnoses that may be missing, and/or the like.

An apparatus is provided for utilizing a trained encoder to encode, as predefined sized vectors, healthcare claims comprising a variable number of service lines. The apparatus may comprise at least one processor and at least one memory including computer program code, the at least one memory and the computer program code configured to, with the processor, cause the apparatus to at least receive a claim-level record associated with a healthcare claim, wherein the claim-level record comprises attributes describing a patient visit for healthcare services, and receive one or more service lines related to the claim-level record, wherein each service line comprises attributes describing services rendered during the patient visit. The at least one memory and the computer program code may be configured to, with the processor, cause the apparatus to embed claim-level features from the claim-level record to generate a claim-level vector, and embed service line features from each of the service lines to generate a service line vector for each service line. The at least one memory and the computer program code may be configured to, with the processor, cause the apparatus to combine the claim-level vector with the one or more service line vectors to generate a predefined sized vector representative of the healthcare claim, the predefined sized vector reflecting hierarchical relationships between at least some of the service lines and the claim-level record, enabling a prediction engine to generate predictions.

According to certain embodiments, the at least one memory and the computer program code are further configured to, with the processor, cause the apparatus to at least train the encoder by inputting a plurality of training healthcare claims, each training healthcare claim comprising a claim-level record and one or more services lines related to the claim-level record, and each training healthcare claim further comprising a confirmed characteristic. Each of the training healthcare claims may have an associated predefined sized vector that, when plotted on an embedding space, is positioned closer to predefined sized vectors representative of other healthcare claims comprising more similar characteristics, relative to other predefined sized vectors representative of other healthcare claims comprising less similar characteristics.

A method is provided for utilizing a trained encoder to encode, as predefined sized vectors, healthcare claims comprising a variable number of service lines. The method may include receiving a claim-level record associated with a healthcare claim, wherein the claim-level record comprises attributes describing a patient visit for healthcare services, and receiving one or more service lines related to the claim-level record, wherein each service line comprises attributes describing services rendered during the patient visit. According to example embodiments, the method includes embedding, with at least a processor, claim-level features from the claim-level record to generate a claim-level vector, and embedding service line features from each of the service lines to generate a service line vector for each service line. The method may include combining the claim-level vector with the one or more service line vectors to generate a predefined sized vector representative of the healthcare claim, the predefined sized vector reflecting hierarchical relationships between at least some of the service lines and the claim-level record, enabling a prediction engine to generate predictions.

According to certain example embodiments, the method further comprises training the encoder by inputting a plurality of training healthcare claims, each training healthcare claim comprising a claim-level record and one or more services lines related to the claim-level record, and each training healthcare claim further comprising a confirmed characteristic. According to some embodiments, each of the training healthcare claims has an associated predefined sized vector that, when plotted on an embedding space, is positioned closer to predefined sized vectors representative of other healthcare claims comprising more similar characteristics, relative to other predefined sized vectors representative of other healthcare claims comprising less similar characteristics.

A computer program product is provided comprising at least one non-transitory computer-readable storage medium having computer-executable program code instructions stored therein, the computer-executable program code instructions comprising program code instructions to receive a claim-level record associated with a healthcare claim, wherein the claim-level record comprises attributes describing a patient visit for healthcare services, and receive one or more service lines related to the claim-level record, wherein each service line comprises attributes describing services rendered during the patient visit. The computer-executable program code instructions may further comprise program code instructions to embed claim-level features from the claim-level record to generate a claim-level vector, and embed service line features from each of the service lines to generate a service line vector for each service line. The computer-executable program code instructions may further comprise program code instructions to combine the claim-level vector with the one or more service line vectors to generate a predefined sized vector representative of the healthcare claim, the predefined sized vector reflecting hierarchical relationships between at least some of the service lines and the claim-level record, enabling a prediction engine to generate predictions.

An apparatus is provided for utilizing a trained encoder to encode, as predefined sized vectors, healthcare claims comprising a variable number of service lines. The apparatus may include means for receiving a claim-level record associated with a healthcare claim, wherein the claim-level record comprises attributes describing a patient visit for healthcare services, and means for receiving one or more service lines related to the claim-level record, wherein each service line comprises attributes describing services rendered during the patient visit. According to example embodiments, the apparatus may include means for embedding, with at least a processor, claim-level features from the claim-level record to generate a claim-level vector, and means for embedding service line features from each of the service lines to generate a service line vector for each service line. The method may include means for combining the claim-level vector with the one or more service line vectors to generate a predefined sized vector representative of the healthcare claim, the predefined sized vector reflecting hierarchical relationships between at least some of the service lines and the claim-level record, enabling a prediction engine to generate predictions.

According to certain example embodiments, the apparatus further comprises means for training the encoder by inputting a plurality of training healthcare claims, each training healthcare claim comprising a claim-level record and one or more services lines related to the claim-level record, and each training healthcare claim further comprising a confirmed characteristic. According to some embodiments, each of the training healthcare claims has an associated predefined sized vector that, when plotted on an embedding space, is positioned closer to predefined sized vectors representative of other healthcare claims comprising more similar characteristics, relative to other predefined sized vectors representative of other healthcare claims comprising less similar characteristics.

According to some example embodiments, the generated predictions relate to adjudication of at least one of the claim-level record or the one or more service lines and/or relate to information expected in the claim-level record or one or more service lines.

According to certain embodiments, the generated prediction comprises at least one of probability of denial, days to pay, probability of being paid as a diagnosis related group (DRG), allowed amount, denial reason, or missing procedure codes. The claim-level record may comprise at least one of patient information, payer information, or a principal diagnosis code. The service lines may comprise at least one of a procedure code, a procedure modifier, a revenue code, or a type of facility.

According to certain embodiments, embedding the claim-level features from the claim-level record to generate the claim-level vector comprises, for each claim-level feature, generating an N-dimensional claim-level vector. Embedding the claim-level features from the claim-level record to generate the claim-level vector may further include concatenating the N-dimensional claim-level vectors to generate an M*N-dimensional claim-level vector representing the claim header, wherein M represents a number of claim-level features.

According to certain embodiments, embedding the service line features from each of the service lines to generate a service line vector for each service line comprises, for each service line feature, generating an N-dimensional service line vector. Embedding the service line features from each of the service lines to generate a service line vector for each service line may further comprise, for each service line, generating an S*N-dimensional service line vector, wherein S is the number of service line features in each service line. Embedding the service line features from each of the service lines to generate a service line vector for each service line may further comprise generating an L-length sequence of S*N-dimensional service line vectors, wherein L is the number of service lines.

According to certain embodiments, generating the predefined sized vector comprises processing the M*N-dimensional claim-level vector and the L-length sequence of S*N-dimensional service line vectors through neural network layers to (a) identify the hierarchical relationships, and (b) reduce dimensionality to D by generating a D-dimensional claim header vector and L D-dimensional line vectors. Generating the predefined sized vector may further include pooling the L D-dimensional line vectors to generate a D-dimensional service-line vector, and concatenating the D-dimensional claim header vector with the D-dimensional service-line vector to generate the predefined sized vector as a D*2-dimensional vector.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWINGS

Figure 1:
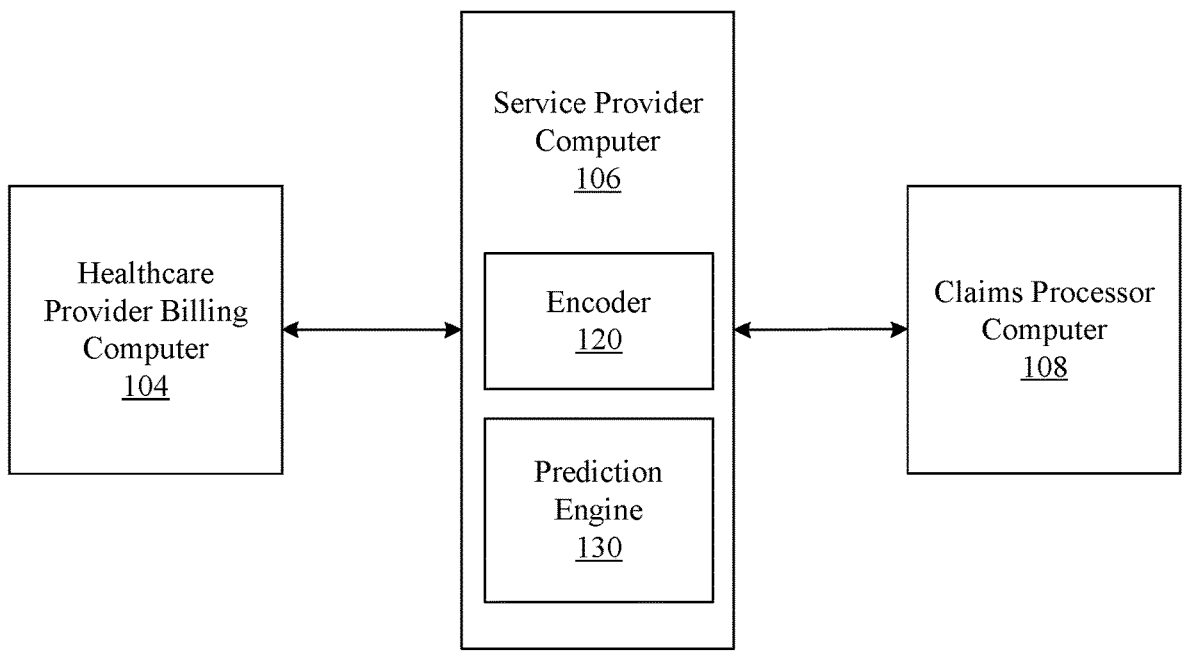
Figure 2:
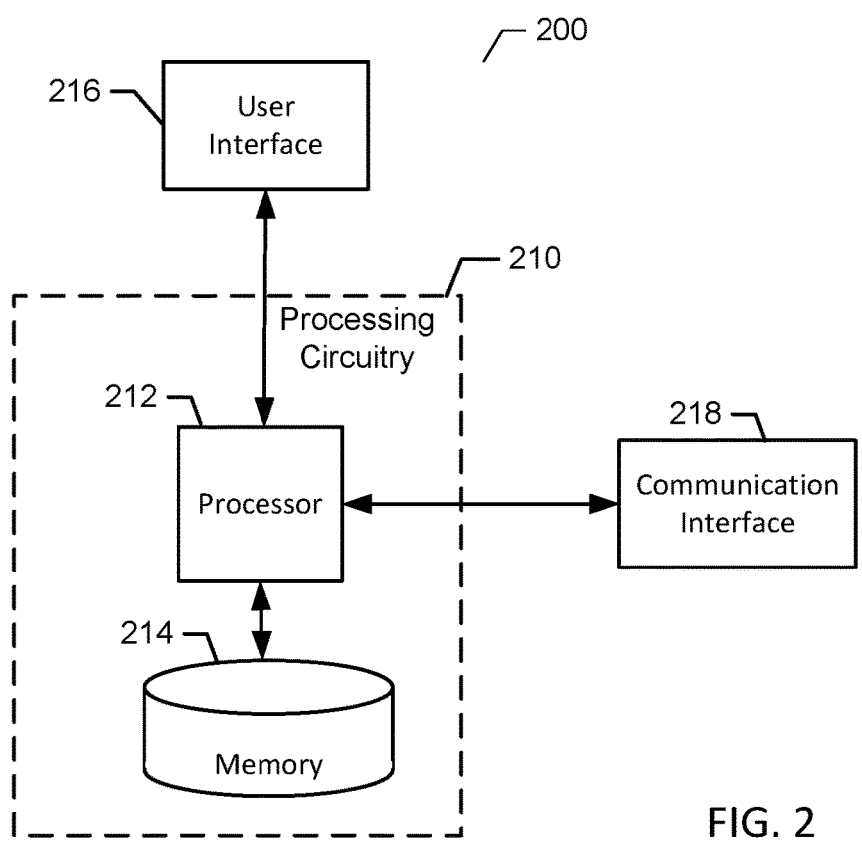

Having thus described embodiments of the invention in general terms, reference will now be made to the accompanying drawings, which are not necessarily drawn to scale, and wherein:

FIG. 1 is an example overview of a system that can be used to practice some example embodiments described herein;

FIG. 2 is an exemplary schematic diagram of an apparatus in accordance with some example embodiments; and FIGS. 3-7 are flowcharts of operations that may be performed in accordance with some example embodiments.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described herein to receive data from another computing device, it will be appreciated that the data may be received directly from the other computing device and/or may be received indirectly via one or more intermediary computing devices, such as, for example, one or more servers, relays, routers, network access points, and/or the like. Similarly, where a computing device is described herein to transmit data to other computing device, it will be appreciated that the data may be sent directly to the other computing device or may be sent to the other computing device via one or more interlinking computing devices, such as, for example, one or more servers, relays, routers, network access points, and/or the like.

FIG. 1 is an overview of a system that can be used to encode healthcare claims and/or make predictions, such as predictions related to expected information in the claim, and/or to likelihood of denial and other outcomes relating to adjudication, according to certain example embodiments described herein. The healthcare provider billing computer 104 may be associated with a healthcare provider, such as, for example, a pharmacy, physician's office, clinic, long-term care facility, hospital, etc., and/or a billing entity associated therewith. For example, a user working in billing for a medical practice and/or the like may enter claim data and/or patient information into a user interface to be submitted to a service provider 106. As another example, a medical coder tasked with reviewing medical records and statements to report pertinent codes and/or other information prior to submitting a claim may utilize healthcare provider billing computer 104 to submit claims for payment (and any pre-adjudication or pre-processing performed by service provider computer 106 described below).

The service provider computer 106 may include, but is not limited to, a processor-driven device that is configured for receiving, processing, and fulfilling requests from the healthcare provider billing computer 104 and/or the claims processor computer 108 (described below), relating to healthcare claims, claims processing, benefits, billing, other healthcare transactions, and/or other related activities. Additionally or alternatively, the service provider computer 106 may be operable to facilitate the receipt, routing, and/or processing of healthcare claims and/or associated responses amongst various components and/or subsystems such as, but not limited to, those depicted in FIG. 1.

For example, the service provider computer 106 may route healthcare claims communicated from the healthcare provider billing computer 104 to a claims processor computer 108, such as that associated with a pharmacy benefits manager (PBM), an insurer, a Medicare or other government healthcare insurance program payor, or other payor. In current systems, the claims processor computer 108 receives healthcare claims, and may queue the claims for processing and adjudication, which may include at least some manual review. In many instances, days or weeks may lapse before a response is returned to the service provider computer 106. In instances in which a claim is denied, the denied claim may need to be forwarded from the service provider computer 106 back to the healthcare provider billing computer 104 for correction.

In this regard, example embodiments of the present disclosure provide an apparatus, method, and computer program product for enabling predictions to be made regarding expected information in the claim and/or claim adjudication, prior to the claim being processed by the claims processor computer 108. Special purpose computer program code, such as an encoder 120, may be configured according to example embodiments described herein to encode a healthcare claim as a predefined sized vector. The predefined sized vector may then be further processed, such as by prediction engine 130, to make predictions. The predictions may be related to subsequent claims processing and/or adjudication, such as but not limited to probability of denial (claim-level or service-level), days to pay, probability of being paid as a diagnosis related group (DRG), allowed amount, denial reason, and/or likelihood and/or identification of missing procedure codes.

Other observations or predictions made by example embodiments may relate to patterns of common services and/or procedure codes relative to claim-level information, or other service lines. For example, certain examinations such as colonoscopies or prostate exams are frequently performed in conjunction with other services such as provision of a liquid drink for the patient to drink prior to the exam. Although the exam and provision of the drink represent separate services, a service line representing the provision of the drink is often present when a service line representing the exam is present in a claim record. As another example, a claim record for child birth may often include several of the same, relatively predictable service lines. The prediction engine 130 may therefore utilize the predefined sized vector representing a healthcare claim to make predictions such as those set forth above, and others.

Predictions relating to the claim may be provided to the healthcare provider billing computer 104 for provision to a user, in real-time and/or near real-time as the information is entered, and/or in real-time and/or near real-time in response to submission of the information to the service provider computer 106. In this regard, the user, such as the biller and/or other user of healthcare provider billing computer 104 may make changes to the claim to provide additional information and/or corrections while they are still working with the file and/or billing record, and before the claim is submitted for adjudication and subject to lengthy review and/or response time.

FIG. 2 is an exemplary schematic diagram of an apparatus 200 in accordance with some example embodiments. Apparatus 200 is a computing device(s) configured for implementing healthcare provider billing computer 104, service provider computer 106, claims processor computer 108, encoder 120 and/or prediction engine 130, according to example embodiments.

Apparatus 200 may at least partially or wholly embody any of the healthcare provider billing computer 104, service provider computer 106, claims processor computer 108, encoder 112 and/or prediction engine 130. Apparatus 200 may therefore implement any of the provider billing computer 104, service provider computer 106, claims processor computer 108, encoder 112 and/or prediction engine 130, in accordance with some example embodiments, or may be implemented as a distributed system that includes any of the provider billing computer 104, service provider computer 106, claims processor computer 108, encoder 112, prediction engine 130, and/or associated network(s).

It should be noted that the components, devices, and elements illustrated in and described with respect to FIG. 2 may not be mandatory and thus some may be omitted in certain embodiments. For example, FIG. 2 illustrates a user interface 216, as described in more detail below, which may be optional in any of the service provider computer 106, claims processor computer 108, encoder 120, and/or prediction engine 130. Additionally, some embodiments may include further or different components, devices, or elements beyond those illustrated in and described with respect to FIG. 2.

Continuing with FIG. 2, processing circuitry 210 may be configured to perform actions in accordance with one or more example embodiments disclosed herein. In this regard, the processing circuitry 210 may be configured to perform and/or control performance of one or more functionalities of apparatus 200 in accordance with various example embodiments. The processing circuitry 210 may be configured to perform data processing, application execution, and/or other processing and management services according to one or more example embodiments. In some embodiments apparatus 200, or a portion(s) or component(s) thereof, such as the processing circuitry 210, may be embodied as or comprise a circuit chip. The circuit chip may constitute means for performing one or more operations for providing the functionalities described herein.

In some example embodiments, the processing circuitry 210 may include a processor 212, and in some embodiments, such as that illustrated in FIG. 2, may further include memory 214. The processing circuitry 210 may be in communication with or otherwise control a user interface 216, and/or a communication interface 218. As such, the processing circuitry 210, such as that included in any of the healthcare provider billing computer 104, service provider computer 106, claims processor computer 108, encoder 120, prediction engine 130, and/or apparatus 200 may be embodied as a circuit chip (e.g., an integrated circuit chip) configured (e.g., with hardware, software, or a combination of hardware and software) to perform operations described herein.

The processor 212 may be embodied in a number of different ways. For example, the processor 212 may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor 212 may comprise a plurality of processors. The plurality of processors may be in operative communication with each other and may be collectively configured to perform one or more functionalities of apparatus 200 as described herein. The plurality of processors may be embodied on a single computing device or distributed across a plurality of computing devices collectively configured to function as healthcare provider billing computer 104, service provider computer 106, claims processor computer 108, encoder 120, prediction engine 130, and/or apparatus 200. In some example embodiments, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry—in the form of processing circuitry 210) capable of performing operations according to embodiments of the present invention while configured accordingly. Thus, for example, when the processor 212 is embodied as an ASIC, FPGA, or the like, the processor 212 may be specifically configured hardware for conducting the operations described herein. Alternatively, as another example, when the processor 212 is embodied as an executor of software instructions, the instructions may specifically configure the processor 212 to perform one or more operations described herein.

In some example embodiments, the memory 214 may include one or more non-transitory memory devices such as, for example, volatile and/or non-volatile memory that may be either fixed or removable. In this regard, the memory 214 may comprise a non-transitory computer-readable storage medium. It will be appreciated that while the memory 214 is illustrated as a single memory, the memory 214 may comprise a plurality of memories. The plurality of memories may be embodied on a single computing device or may be distributed across a plurality of computing devices. The memory 214 may be configured to store information, data, applications, computer program code, instructions and/or the like for enabling apparatus 200 to carry out various functions in accordance with one or more example embodiments. For example, when apparatus 200 is implemented as service provider computer 106, encoder 120, and/or prediction engine 130, memory 214 may be configured to store computer program code for performing corresponding functions thereof, as described herein according to example embodiments. Specifically, the memory 214 may comprise a neural network, trained by example embodiments, and utilized by the encoder 120 to encode healthcare claims, as described in further detail below. The memory 214 may be further configured to store embedding spaces to be used by the prediction engine 130 to make predictions and/or predict characteristics regarding the healthcare claims, as described in further detail below.

Still further, memory 214 may be configured to store routing tables, that facilitate determining the destination of communications received from a healthcare provider billing computer 104, and/or claims processor computer 108. Memory 214 may further include reconciliation tables for tracking the healthcare claims received from the healthcare provider 104, and reconciling them with responses received from claims processor computer 108. The memory 214 may be modified as described herein, to reformat healthcare claims with additional information received, determined and/or generated according to example embodiments.

The memory 214 may be further configured to buffer input data for processing by the processor 212. Additionally or alternatively, the memory 214 may be configured to store instructions for execution by the processor 212. In some embodiments, the memory 214 may include one or more databases that may store a variety of files, contents, or data sets. Among the contents of the memory 214, applications may be stored for execution by the processor 212 to carry out the functionality associated with each respective application. In some cases, the memory 214 may be in communication with one or more of the processor 212, user interface 216, and/or communication interface 218, for passing information among components of apparatus 200.

The optional user interface 216 may be in communication with the processing circuitry 210 to receive an indication of a user input at the user interface 216 and/or to provide an audible, visual, mechanical, or other output to the user. As such, the user interface 216 may include, for example, a keyboard, a mouse, a display, a touch screen display, a microphone, a speaker, and/or other input/output mechanisms. As such, in embodiments in which apparatus 200 implemented as the healthcare provider billing computer 104, the user interface 216 may, in some example embodiments, provide means for user entry of insurance information, patient information, details relating to a patient bill, service, healthcare claim, and/or the like. The user interface 216 may be further configured to provide feedback to the user regarding predictions based on the information input at the healthcare provider billing computer 104. In some example embodiments, aspects of user interface 216 may be limited or the user interface 216 may not be present.

The communication interface 218 may include one or more interface mechanisms for enabling communication with other devices and/or networks. In some cases, the communication interface 218 may be any means such as a device or circuitry embodied in either hardware, or a combination of hardware and software that is configured to receive and/or transmit data from/to a network and/or any other device or module in communication with the processing circuitry 210. By way of example, the communication interface 218 may be configured to enable communication amongst any of healthcare provider billing computer 104, service provider computer 106, claims processor computer 108, encoder 120, prediction engine 130, and/or apparatus 200 over a network. Accordingly, the communication interface 218 may, for example, include supporting hardware and/or software for enabling wireless and/or wireline communications via cable, digital subscriber line (DSL), universal serial bus (USB), Ethernet, or other methods.

The network, such as the network in which any of the systems of FIGS. 1, 2, or components thereof or components described herein may operate, (e.g., healthcare provider billing computer 104, service provider computer 106, claims processor computer 108, encoder 120, prediction engine 130, apparatus 200, and/or the like) may include a local area network, the Internet, any other form of a network, or in any combination thereof, including proprietary private and semi-private networks and public networks. The network may comprise a wired network and/or a wireless network (e.g., a cellular network, wireless local area network, wireless wide area network, some combination thereof, and/or the like).

Figure 3:
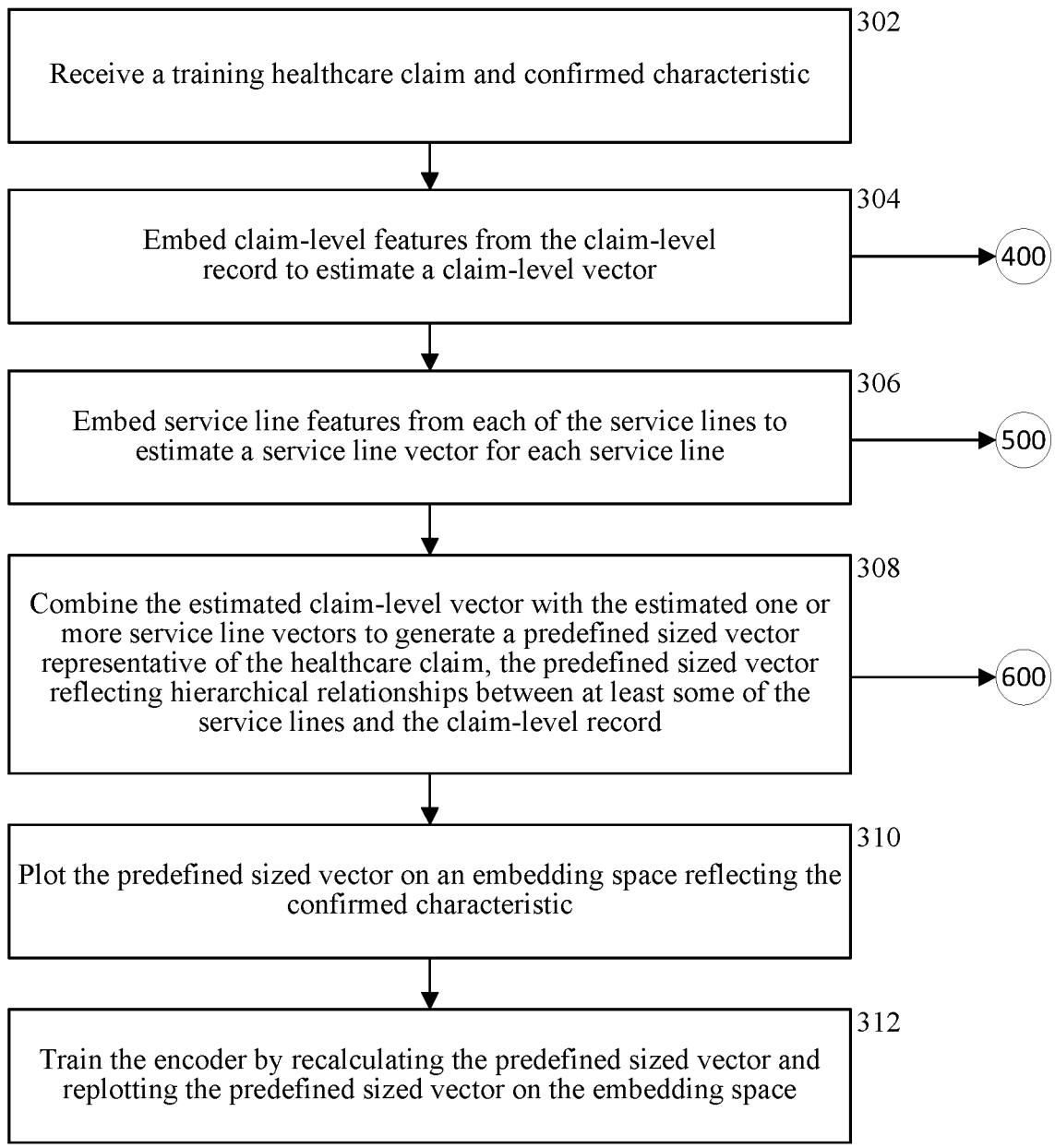

Having now described an example apparatus for implementing example embodiments, FIG. 3 is a flowchart illustrating example operations of an apparatus 200, according to some example embodiments. The operations of FIG. 3 may be performed by apparatus 200, such as with the service provider computer 106, encoder 120, and/or the like, and may be used to train the encoder 120.

As shown by operation 302, apparatus 200 may include means, such as processor 212, memory 214, communication interface 218, and/or the like, for receiving a training healthcare claim and confirmed characteristic. The training healthcare claim may be one of a plurality of historical claims stored and/or collected over a period of time (e.g., months or years).

According to some embodiments, the characteristic may relate to a confirmed outcome regarding adjudication. In this regard, the service provider computer 106 may store claims submitted by the healthcare provider billing computer 104 and reconcile the submitted claims with associated paid claims and/or received responses from the claims processor computer 108. The confirmed outcomes regarding adjudication may include any process related to pre-adjudication, adjudication, or post-adjudication processes. Some outcomes may include, but are not limited to, approval or denial at the claim-level and/or any service line, number of days until the claim was paid, whether the claim was treated or paid as a diagnosis related group (DRG), the allowed amount, denial reasons, and/or the like.

According to some embodiments, the confirmed characteristics may be related to expected information in the healthcare claim, such as service codes that often appear in the same claims, service codes that often appear with particular diagnoses, and/or the like. In this regard, the confirmed characteristic may be derived from the claim itself.

As introduced above, a healthcare claim may include one claim-level record, and a variable number of service lines. A claim-level record may comprise any number of fields, such as but not limited to:
    payer_id
    principal diagnosis code
    principal institutional procedure code
    patient gender
    facility code Service-lines comprised by or associated with the healthcare claim and the claim-level record may comprise any number of fields, such as but not limited to:
    procedure code
    procedure modifiers
    revenue code The fields in the claim-level record and service-lines and corresponding responses from the claims processor computer 108 may correspond to fields in the American National Standards Institute (ANSI) X12 Electronic Data Interchange (EDI) 835 and/or 837 transactions sets. The EDI 837 transaction set includes definitions or formats of data to be sent by the healthcare provider billing computer 104 and/or service provide computer 106 to the claims processor computer 108 for adjudication and/or processing. The EDI 835 transaction set includes definitions or formats of data to be sent from the claims processor computer 108 regarding a response, including payment, denial, any/or the like. In this regard, the training healthcare claims may be in the format defined by the EDI 837, and responses including confirmed outcomes (e.g., characteristic) regarding adjudication may be in a format defined by the EDI 835. The training healthcare claims and corresponding characteristics may be stored in a database and/or memory 214.

As shown by operation 304, apparatus 200 may include means, such as processor 212, memory 214, encoder 120 and/or the like, for embedding claim-level features from the claim-level record to estimate a claim-level vector. According to certain embodiments, the claim-level features may be identified as a subset of fields or attributes of the claim-record. For example, the claim-level features may include a subset of fields defined by EDI 837. The claim-level features initially selected may be selected at random, then fine-tuned and weighted according to the training and machine learning process described below. The computer program code may then be trained to identify the claim-level features and generate claim-level vectors that are likely to yield relatively predictable correlations to the confirmed characteristics. Process 400 of FIG. 4 describes the generation of a claim-level vector in more detail.

Continuing with operation 306, apparatus 200 may include means, such as processor 212, memory 214, encoder 120 and/or the like, for embedding service line features from each of the services lines to estimate a service line vector for each service line. Similar to the claim-level embedding, example embodiments identify a subset of features from service-lines, which may correspond to fields or attributes of the service lines. The subset of features from the service lines may also be initially selected at random and adjusted and weighted through the training process. The computer program code may then be trained to identify service line features and generate service line vectors that are likely to yield predictions with a reasonable (satisfying a threshold level) of confidence. Process 500 of FIG. 5 describes the generation of service line vectors in more detail.

In operation 308, apparatus 200 may include means, such as processor 212, memory 214, communication interface 218, encoder 120 and/or the like, for combining the estimated claim-level vector with the one or more estimated service line vectors to generate a predefined sized vector representative of the healthcare claim. Example embodiments combine the vectors such that the resultant predefined sized vector reflects hierarchical relationships between at least some of the service lines and the claim-level record. The hierarchical relationships may refer to relationships inferred between service lines and their respective claim-level record. As such, example embodiments combine claim-level attributes with line-level attributes such that context is not lost nor important information destroyed. For example, certain service lines may have different meaning or significance when they appear with certain claim-level diagnoses. Predictions may be made relating to a service-line based on information from the claim-level record or other service lines. In this regard, example embodiments capture the hierarchical relationships through machine learning, that may otherwise only be observed by extensive manual review by a skilled medical coder, human claim adjudicator and/or the like. The machine learning algorithms utilized by example embodiments may include, but are not limited to supervised learning, and/or semi-supervised learning with data augmentation, for example.

Figure 6:
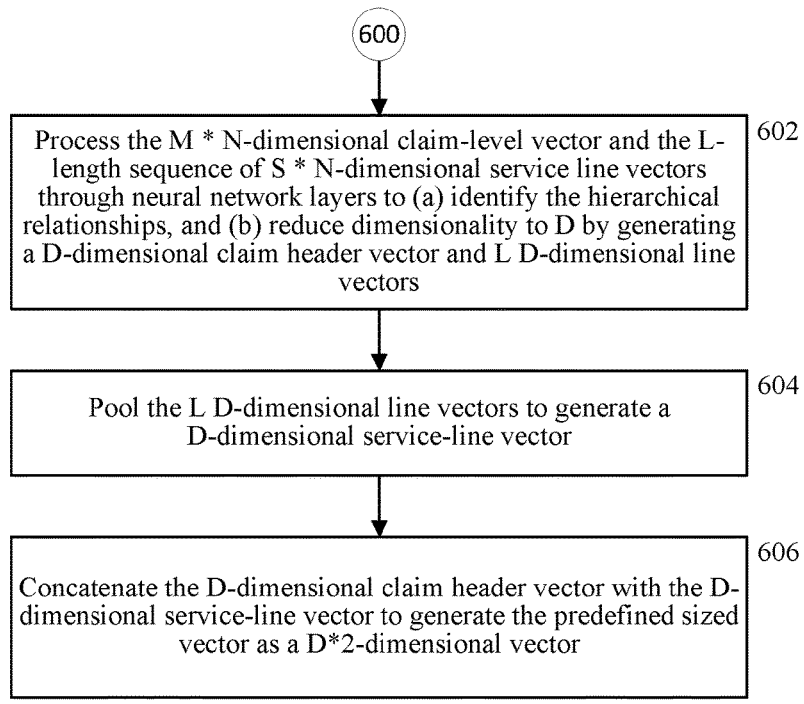

Process 600 of FIG. 6 describes the combination of the claim-level vector with the service line vectors in more detail.

Representing the healthcare claim as a vector of a predefined size, regardless of length or size of the healthcare claim (e.g., number of service lines) enables for example embodiments to efficiently plot vectors representing different healthcare claims on a uniform embedding space for a particular prediction type, in order to train the neural network to generate more accurate vector representations of healthcare claims, where more accurate representations produce more accurate predictions than less accurate vector representations. In this regard, example embodiments may be implemented and trained such that the number of service lines is variable or unknown for each healthcare claim, but the resultant predefined sized vector is fixed at runtime (e.g., predefined independent of the claim length and/or service line count). The term "runtime" is referenced to emphasize that the size of the predefined sized vector may be altered on occasion if so desired, such as by changing the computer program code on memory 214, but that the size is not dependent or variable based on the claim length and/or number of service lines.

In operation 310, apparatus 200 may include means, such as processor 212, memory 214, encoder 120 and/or the like, for plotting the predefined sized vector on an embedding space reflecting the confirmed characteristic. For a given type of prediction, example embodiments may build an embedding space for plotting the training healthcare claims with their associated confirmed characteristic. For example, example embodiments may utilize one embedding space and corresponding neural network for generating predefined sized vectors to predict claim-level approval or denial, but another separate embedding space and corresponding neural network for predicting days to pay. Different data or fields within the healthcare claims (e.g., claim level record and/or services lines) may be more or less relevant to the type of prediction being made, relative the other data or fields.

In any event, defining and developing an embedding space for each prediction type enables example embodiments to represent pairs of the predefined sized vectors and corresponding confirmed outcomes with a notion of perceived proximity and/or distance relative to other pairs of predefined sized vectors and confirmed outcomes. Having a confirmed characteristic(s) for each training healthcare claim enables example embodiments to quantify the characteristics in such a way that the vectors and outcomes can be plotted on the embedding space. In this regard, training healthcare claims with similar outcomes are plotted near each other, and example embodiments can train the neural network to generate a predefined sized vector for a particular training healthcare claim that, when plotted on an embedding space, is positioned closer to predefined sized vectors representative of other healthcare claims comprising more similar confirmed characteristics, relative to other predefined sized vectors representative of other healthcare claims comprising less similar confirmed characteristics.

In operation 312, apparatus 200 may include means, such as processor 212, memory 214, communication interface 218, and/or the like, for training the encoder, such as encoder 120, by recalculating the predefined sized vector and replotting the predefined sized vector on the embedding space. In this regard, the operations of FIG. 3 may be repeated for a plurality of different training healthcare claims, and even for the same training healthcare claim, such that the training healthcare claims more similar to each other become plotted closer to each other than those that are less similar, as the neural network is trained. The encoder 120 is therefore trained by the neural network to optimize the predefined sized vector to enable reliable (at least satisfying a calculated confidence level, for example) predictions to be made by the prediction engine 130.

Training the neural network as illustrated in the flowchart of FIG. 3 may be performed by a variety of machine learning techniques. The claim-level vectors and service line vectors may be adjusted or fine-tuned in training iterations performed by the neural network, by modifying weights applied in each iteration. The training process may therefore produce an adjusted or fine-tuned resultant predefined sized vector in each iteration, and example embodiments can determine the reliability with which the estimated predefined sized vector yields a correct characteristic. Example embodiments may calculate and monitor a gradient descent algorithm to determine convergence and therefore the optimal and/or determined weights for the neural network and/or model for a particular prediction type.

Figure 4:
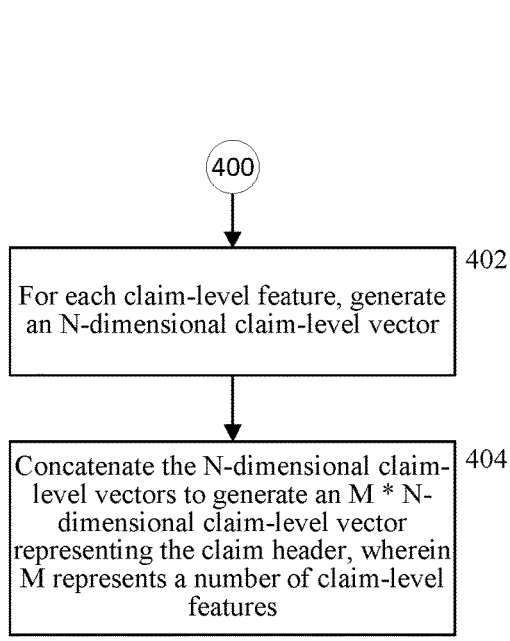

FIG. 4 is a flowchart of process 400 illustrating operations for generating a claim-level vector according to example embodiments. At operation 402, apparatus 200 200 may include means, such as processor 212, memory 214, encoder 120, and/or the like, for generating, for each claim-level feature, an N-dimensional claim-level vector. According to example embodiments, N may be defined as a hyperparameter of the encoder 120. N is generally constant for all iterations and/or claims for a given prediction type and/or model. Different models used for different types of predictions may be trained with different values for N. For example, N may be larger for prediction types having an associated model with greater capacity and/or complexity relative to a model with lesser capacity and/or complexity. In some embodiments, an initial or current value of N may be arbitrarily chosen before training, but may optionally be changed by configuring according to the performance of the training. Different values of N may be evaluated and selected based on balancing performance and cost. However, because example embodiments aim to generate a predefined sized vector regardless of the claim size and/or service line count, N is not changed according to claim size. Rather, N is generally constant for a given model, unless specifically altered in memory 214 such as by specific direction from a user such as a computer program developer.

The claim-level features may be fields or attributes of the claim-level record identified through the machine learning process identified as useful or pertinent in making certain types of predictions. For example, the payer_id field may be useful in predicting days to pay, but the facility code made be not important or may be less important. The claim-level features learned through machine learning may also vary based on the dataset. For instance, if a particular healthcare provider computer 104 provides claims that include only inpatient hospital claims, and all the facility code values are the same, example embodiments may not utilize such fields as the claim-level features, because the fields will likely not provide a benefit in making predictions.

In operation 404, apparatus 200 may include means, such as processor 212, memory 214, encoder 120, and/or the like, for concatenating the N-dimensional claim-level vectors to generate an M*N-dimensional claim-level vector representing the claim header, wherein M represents a number of claim-level features.

Figure 5:
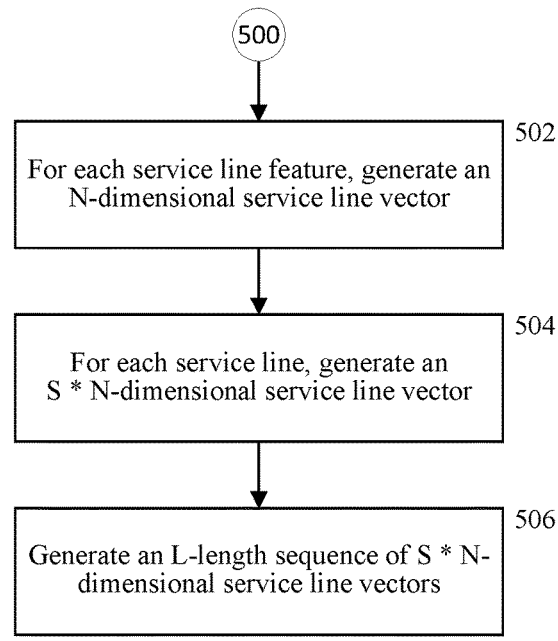

FIG. 5 is a flowchart of process 500 illustrating operations for generating service line vectors. In operation 502, apparatus 200 may include means, such as processor 212, memory 214, encoder 120, and/or the like, for generating, for each service line feature, an N-dimensional service line vector. In operation 504, apparatus 200 may include means, such as processor 212, memory 214, encoder 120, and/or the like, for generating an S*N-dimensional service line vector for each service line. S may be considered the number of service line features in each service line. In operation 506, apparatus 200 may include means, such as processor 212, memory 214, encoder 120, and/or the like, for generating an L-length sequence of S*N-dimensional service line vectors. L may therefore be the number of service lines related to the claim-level record. The L-length sequence may be generated by concatenating the S*N-dimensional vectors.

FIG. 6 is a flowchart of process 500 illustrating operations for generating the predefined sized vector. At operation 602, apparatus 200 may include means, such as processor 212, memory 214, encoder 120, and/or the like, for processing the M*N-dimensional claim-level vector and the L-length sequence of S*N-dimensional service line vectors through neural network layers to (a) identify the hierarchical relationships, and (b) reduce dimensionality to D by generating a D-dimensional claim header vector and L D-dimensional line vectors.

In operation 604, apparatus 200 may include means, such as processor 212, memory 214, encoder 120, and/or the like, for pooling the L D-dimensional line vectors to generate a single D-dimensional service-line vector. In this regard, the pooling process determines which service lines, and the data therein, are more important or useful in making certain predictions. In some examples, the pooling process may learn from training, which service lines in certain positions within a list of service lines are more valuable or useful than others. The pooling process may be implemented as a sequence reduction process with AveragePooling and/or MaxPooling. The pooling process reduces spatial dimensions to ultimately enable concatenation to generate a predefined sized vector (described below) and thereby improve performance and enable efficient training and processing of the claim data.

It will be appreciated that pooling the L D-dimensional line vectors as described above may be modified by performing additional or alternative sequence reduction methods. There may be different types of pooling (e.g. MaxPooling and AveragePooling). MaxPooling takes the maximum value for each dimension across the sequence, while AveragePooling may produce the average value for each dimension across the sequence. For instance, if there was a sequence of 2 2-dimensional vectors: [[1, 4], [3, 2]], MaxPooling would produce 1 2-dimensional vector: [3, 4], and AveragePooling for the same case would produce [2, 3]. Other sequence reduction methods include summing the vectors, or attention mechanisms (weighted sums).

In operation 606, apparatus 200 may include means, such as processor 212, memory 214, encoder 120, and/or the like, for concatenating the D-dimensional claim header vector with the D-dimensional service-line vector to generate the predefined sized vector as a D*2-dimensional vector. In certain example embodiments D is predefined as an amount determined to produce a reliable vector for making certain types of predictions. For example, D may be determined as 32, such that the predefined size vector is a 64-dimensional vector. Although D is generally constant once the encoder 120 is trained as in use to encode new claims, D may be initially determined or configured empirically while considering factors such as model complexity and/or cost. Different encoders 120 may use different sized vectors depending on the prediction type and/or model. Accordingly, D is generally constant for a given model, unless specifically altered in memory 214 such as by specific direction from a user such as a computer program developer.

As described with respect to operations 310 and 312, once a vector of the predefined size has been generated for a particular healthcare claim, example embodiments plot the vector on an embedding space for the type of prediction, and train the encoder 120 and neural network to generate more accurate vector representations of healthcare claims for the prediction type. The neural network may be trained with thousands of healthcare claims and their confirmed characteristics.

Figure 7:
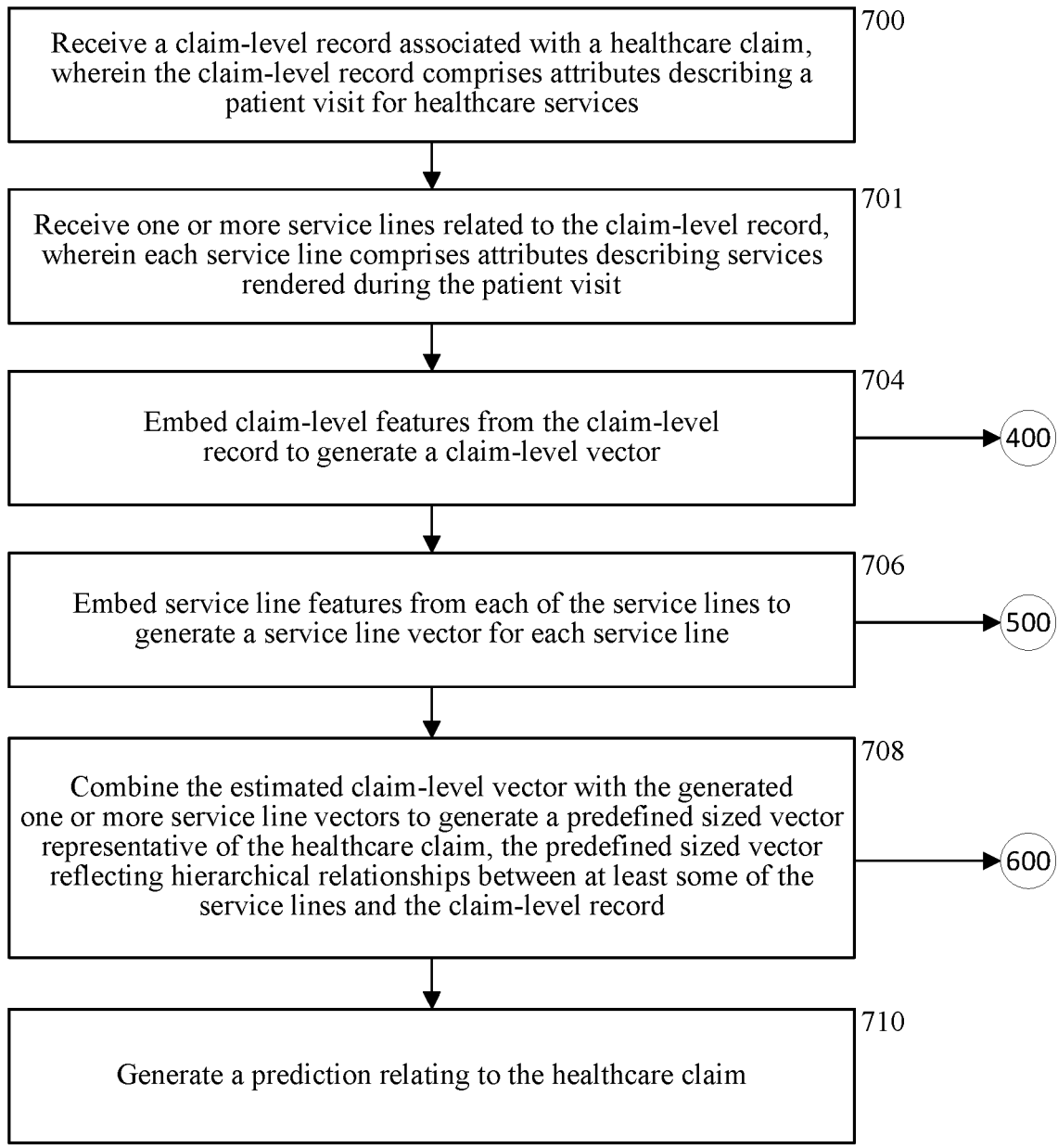

Once trained, apparatus 200, may include means, such as processor 212, memory 214, encoder 120, and/or the like, for receiving healthcare claims that do not yet have an associated adjudication outcome or response. In this regard, new healthcare claims may be submitted from a healthcare provider billing computer 104 to the service provider computer 106. The trained encoder 120 may then encode the healthcare claim as a predefined size vector, and the prediction engine 130 may use the predefined sized vector to make predictions regarding adjudication, potential missing service codes, and/or the like. This process is illustrated in FIG. 7.

In operation 700, apparatus 200, may include means, such as processor 212, memory 214, communication interface 218, and/or the like, for receiving a claim-level record associated with a healthcare claim, wherein the claim-level record comprises attributes describing a patient visit for healthcare services. In operation 701, apparatus 200, may include means, such as processor 212, memory 214, communication interface 218, and/or the like, for receiving one or more service lines related to the claim-level record, wherein each service line comprises attributes describing services rendered during the patient visit. It will be appreciated that the healthcare claim may be received and/or accessed on a database, for example, as a single record comprising the claim-level record and related services lines, but is illustrated as operations 700 and 701 for clarity.

Operations 704, 706, and 708 are similar to respective operations 304, 306, 308, except that operations 304, 306, 308 estimate their respective vectors and are reiterated with potentially different weights during a machine learning process such that the respective vectors are adjusted and fine-tuned as the encoder 120 is trained using the respective confirmed characteristics of the training samples. Operations 704, 706, and 708 are similarly performed, but by the trained encoder 120, such that the embeddings need not be repeated or adjusted. Rather, the trained encoder 120 is trained to efficiently generate a reasonably accurate (e.g., satisfying a threshold level of confidence) vector representation of the healthcare claim.

In this regard, it will be appreciated that the operations of FIGS. 4, 5 and 6 may be performed as referenced from FIG. 3, to train the encoder 120, and/or while implementing a "non-training" embodiment, such as described with reference to FIG. 7, to generate predefined sized vector representations of healthcare claims for which the characteristics are not confirmed, are not yet confirmed, or are unknown at the time of submission. The process of FIG. 3, relating to training, and the process of FIG. 7, relating to execution with a trained encoder, are provided separately for clarity. However, it will be appreciated that this separation of disclosure does not preclude example embodiments, such as encoder 120, from being further trained during the performance of operations of FIG. 7. For example, even though adjudication outcomes may not initially be available when a healthcare claim is submitted to the service provider computer 106, the claims could be processed according to FIG. 7, enabling a prediction to be made, but may also be utilized in a training process once the adjudication is performed and an adjudication response is received from claims processor computer 108. Similarly, characteristics regarding the claims (such as service lines expected to be present) may be derived from the claims such that an adjudication response is not necessarily needed to train a neural network related to such a prediction. In this regard, example embodiments may be further trained as the service provider computer 106 processes healthcare claims and generates the corresponding predefined sized vectors.

Continuing with the description of FIG. 7, in operation 704, apparatus 200, may include means, such as processor 212, memory 214, encoder 120 (e.g., the trained encoder 120), and/or the like, for embedding claim-level features from the claim-level record to generate a claim-level vector. Process 400 of FIG. 4, described above, describes the generation of a claim-level vector in more detail.

In operation 706, apparatus 200, may include means, such as processor 212, memory 214, encoder 120 (e.g., the trained encoder 120), and/or the like, for embedding service line features from each of the service lines to generate a service line vector for each service line. Process 500 of FIG. 5, described above, describes the generation of service line vectors in more detail.

In operation 708, apparatus 200, may include means, such as processor 212, memory 214, encoder 120 (e.g., the trained encoder 120), and/or the like, for combining the estimated claim-level vector with the one or more generated service line vectors to generate a predefined sized vector representative of the healthcare claim, the predefined sized vector reflecting hierarchical relationships between at least some of the service lines and the claim-level record. Process 600 of FIG. 6, described above, describes the combination of the claim-level vector with the service line vectors in more detail.

After the predefined size vector representative of the healthcare claim is generated, a prediction engine, such as prediction engine 130 may be capable of processing and/or utilizing the predefined size vector in making a prediction regarding adjudication outcomes and/or other characteristic of the claims. In operation 710, apparatus 200, may include means, such as processor 212, memory 214, prediction engine 130, and/or the like, for generating a prediction relating to the healthcare claim. The prediction may relate to any of the characteristics described herein, such as but not limited to predictions regarding adjudication outcome, and/or expected diagnoses and/or services.

Example embodiments may therefore enable the prediction engine to generate predictions in real-time or near real-time relative to being submitted by the healthcare provider billing computer 104. In this regard, a biller or other user may be notified in real-time or near real-time, of claims likely to be rejected or denied, claims predicted as needing a relatively longer time for adjudication, relative to others, and/or the like. In some embodiments, the prediction engine 130 may identify service lines (or procedure codes) frequently found within other similar claims, but missing from a particular claim. In any event, a user of the healthcare provider billing computer 104 may be alerted of potential issues and may be prompted to make corrections or changes to the healthcare claim, thereby limiting or reducing potential denials, improving the wait time for adjudication and payment, and/or the like.

Enabling the prediction engine 130 to generate such predictions in real-time or near real-time may provide improved customer service, as denials, rejections and other problems may be reduced or avoided such that the patient is not impacted by such scenarios. Additionally, example embodiments reduce the amount of memory and processing resources otherwise utilized to communicate and track rejections and denials. Similarly, example embodiments may reduce and/or eliminate the need for resubmission of claims. This may therefore reduce the resources expended, such as memory and/or processing power, that may otherwise be required to facilitate the resubmission (and possibly numerous resubmissions) of the same claim, as well as the associated rerouting, and reprocessing of the resubmitted claim(s) throughout the various components described herein. Accordingly, example embodiments described herein further improve the technical efficiency of systems implementing and/or employing such embodiments.

Implementing example embodiments with a trained encoder 120, and/or by training the encoder 120 provides further technical advantages over any such comparative manual processes. Once a model has been trained using historical claims data, the same model (e.g., encoder 120) can be used with only slight, incremental updates as laws, rules and/or policies change. In this regard, historical claim data can be continuously or routinely fed into example embodiments such that neural network is trained to learn new patterns in claim adjudication and/or claim/service hierarchies. Prediction engines, such as prediction engine 130 can evolve and be further developed to make new predictions requested by clients such as users of healthcare provider billing computer 140.

Using a predefined sized vector not only enables reasonably accurate (within a certain confidence level) predictions in which hierarchical relationships are preserved, but enables such predictions to be made in an efficient manner. Other implementations that have attempted to use machine learning to make predictions about healthcare claims may require hand engineering of many features and/or utilize thousands of features which is inefficient in terms of machine learning. Utilizing such a large dataset would result in extremely slow and inefficient training. A concept in machine learning called recursive dimensionality demonstrates that the more features identified, the harder it is to get an accurate robust model. Training neural networks according to example embodiments to generate predefined sized vectors enable example embodiments to use embeddings to reduce the number of features otherwise present in a claim. Limiting the vector to the predefined sized, as set forth in example embodiments, ensures that the model can be trained in an efficient manner.

It will be appreciated that the figures are each provided as examples and should not be construed to narrow the scope or spirit of the disclosure in any way. In this regard, the scope of the disclosure encompasses many potential embodiments in addition to those illustrated and described herein. Numerous other configurations may also be used to implement embodiments of the present invention.

FIGS. 3-7 illustrate operations of a method, apparatus, and computer program product according to some example embodiments. It will be understood that each operation of the flowchart or diagrams, and combinations of operations in the flowchart or diagrams, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 214) storing instructions executable by a processor in the computing device (for example, by processor 212). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, apparatus 200) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer program products may also be loaded onto a computer or other programmable apparatus (for example, apparatus 200 and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. An apparatus for utilizing a trained encoder to encode, as predefined sized vectors, healthcare claims comprising a variable number of service lines, the apparatus comprising at least one processor and at least one memory including computer program code, the at least one memory and the computer program code configured to, with the processor, cause the apparatus to at least:

receive a claim-level record associated with a healthcare claim, wherein the claim-level record comprises attributes describing a patient visit for healthcare services;

receive one or more service lines related to the claim-level record, wherein each service line comprises attributes describing services rendered during the patient visit;

embed claim-level features from the claim-level record to generate a claim-level vector;

embed service line features from each of the service lines to generate a service line vector for each service line;

combine the claim-level vector with the one or more service line vectors to generate a predefined sized vector representative of the healthcare claim, the predefined sized vector reflecting hierarchical relationships between at least some of the service lines and the claim-level record, enabling a prediction engine to generate predictions; and train the encoder by inputting a plurality of training healthcare claims, each training healthcare claim comprising a claim-level record and one or more services lines related to the claim-level record, and each training healthcare claim further comprising a confirmed characteristic;

wherein each of the training healthcare claims has an associated predefined sized vector that, when plotted on an embedding space, is positioned closer to predefined sized vectors representative of other healthcare claims comprising more similar characteristics, relative to other predefined sized vectors representative of other healthcare claims comprising less similar characteristics.

2. The apparatus of claim 1, wherein the generated predictions relate to adjudication of at least one of the claim-level record or the one or more service lines.

3. The apparatus of claim 1, wherein the generated predictions relate to information expected in the claim-level record or one or more service lines.

4. The apparatus of claim 1, wherein the generated prediction comprises at least one of:
probability of denial;
days to pay;
probability of being paid as a diagnosis related group (DRG);
allowed amount;
denial reason; or
missing procedure codes.

5. The apparatus of claim 1, wherein the claim-level record comprises at least one of patient information, payer information, or a principal diagnosis code.

6. The apparatus of claim 1, wherein at least one of the service lines comprises at least one of a procedure code, a procedure modifier, a revenue code, or a type of facility.

7. The apparatus of claim 1,
wherein embedding the claim-level features from the claim-level record to generate the claim-level vector comprises:
for each claim-level feature, generating an N-dimensional claim-level vector; and
concatenating the N-dimensional claim-level vectors to generate an M*N-dimensional claim-level vector representing the claim header, wherein M represents a number of claim-level features,
wherein embedding the service line service line features from each of the service lines to generate a service line vector for each service line comprises:
for each service line feature, generating an N-dimensional service line vector; and
for each service line, generate an S*N-dimensional service line vector, wherein S is the number of service line features in each service line;
generate an L-length sequence of S*N-dimensional service line vectors, wherein L is the number of service lines;

wherein generating the predefined sized vector comprises:
processing the M*N-dimensional claim-level vector and the L-length sequence of S*N-dimensional service line vectors through neural network layers to (a) identify the hierarchical relationships, and (b) reduce dimensionality to D by generating a D-dimensional claim header vector and L D-dimensional line vectors;
pooling the L D-dimensional line vectors to generate a D-dimensional service-line vector; and
concatenating the D-dimensional claim header vector with the D-dimensional service-line vector to generate the predefined sized vector as a D*2-dimensional vector.

8. A method for utilizing a trained encoder to encode, as predefined sized vectors, healthcare claims comprising a variable number of service lines, the method comprising:
receiving a claim-level record associated with a healthcare claim, wherein the claim-level record comprises attributes describing a patient visit for healthcare services;
receiving one or more service lines related to the claim-level record, wherein each service line comprises attributes describing services rendered during the patient visit;
embedding, with at least a processor, claim-level features from the claim-level record to generate a claim-level vector;
embedding service line features from each of the service lines to generate a service line vector for each service line;
combining the claim-level vector with the one or more service line vectors to generate a predefined sized vector representative of the healthcare claim, the predefined sized vector reflecting hierarchical relationships between at least some of the service lines and the claim-level record, enabling a prediction engine to generate predictions; and
training the encoder by inputting a plurality of training healthcare claims, each training healthcare claim comprising a claim-level record and one or more services lines related to the claim-level record, and each training healthcare claim further comprising a confirmed characteristic;
wherein each of the training healthcare claims has an associated predefined sized vector that, when plotted on an embedding space, is positioned closer to predefined sized vectors representative of other healthcare claims comprising more similar characteristics, relative to other predefined sized vectors representative of other healthcare claims comprising less similar characteristics.

9. The method of claim 8, wherein the generated predictions relate to adjudication of at least one of the claim-level record or the one or more service lines.

10. The method of claim 8, wherein the generated predictions relate to information expected in the claim-level record or one or more service lines.

11. The method of claim 8, wherein the generated prediction comprises at least one of:
probability of denial;
days to pay;
probability of being paid as a diagnosis related group (DRG);
allowed amount;
denial reason; or
missing procedure codes.

12. The method of claim 8, wherein the claim-level record comprises at least one of patient information, payer information, or a principal diagnosis code.

13. The method of claim 8, wherein at least one of the service lines comprises at least one a procedure code, a procedure modifier, a revenue code, or a type of facility.

14. The method of claim 8, wherein embedding the claim-level features from the claim-level record to generate the claim-level vector comprises:
   for each claim-level feature, generating an N-dimensional claim-level vector; and
   concatenating the N-dimensional claim-level vectors to generate an M*N-dimensional claim-level vector representing the claim header, wherein M represents a number of claim-level features,
   wherein embedding the service line service line features from each of the service lines to generate a service line vector for each service line comprises:
   for each service line feature, generating an N-dimensional service line vector; and
   for each service line, generate an S*N-dimensional service line vector, wherein S is the number of service line features in each service line;
   generate an L-length sequence of S*N-dimensional service line vectors, wherein L is the number of service lines;
   wherein generating the predefined sized vector comprises:
   processing the M*N-dimensional claim-level vector and the L-length sequence of S*N-dimensional service line vectors through neural network layers to (a) identify the hierarchical relationships, and (b) reduce dimensionality to D by generating a D-dimensional claim header vector and L D-dimensional line vectors;
   pooling the L D-dimensional line vectors to generate a D-dimensional service-line vector; and
   concatenating the D-dimensional claim header vector with the D-dimensional service-line vector to generate the predefined sized vector as a D*2-dimensional vector.

15. A computer program product for utilizing a trained encoder to encode, as predefined sized vectors, healthcare claims comprising a variable number of service lines, the computer program product comprising at least one non-transitory computer-readable storage medium having computer-executable program code instructions stored therein, the computer-executable program code instructions comprising program code instructions to:
   receive a claim-level record associated with a healthcare claim, wherein the claim-level record comprises attributes describing a patient visit for healthcare services;
   receive one or more service lines related to the claim-level record, wherein each service line comprises attributes describing services rendered during the patient visit;
   embed claim-level features from the claim-level record to generate a claim-level vector;
   embed service line features from each of the service lines to generate a service line vector for each service line;
   combine the claim-level vector with the one or more service line vectors to generate a predefined sized vector representative of the healthcare claim, the predefined sized vector reflecting hierarchical relationships between at least some of the service lines and the claim-level record, enabling a prediction engine to generate predictions; and
   train the encoder by inputting a plurality of training healthcare claims, each training healthcare claim comprising a claim-level record and one or more services lines related to the claim-level record, and each training healthcare claim further comprising a confirmed characteristic;
   wherein each of the training healthcare claims has an associated predefined sized vector that, when plotted on an embedding space, is positioned closer to predefined sized vectors representative of other healthcare claims comprising more similar characteristics, relative to other predefined sized vectors representative of other healthcare claims comprising less similar characteristics.

16. The computer program product of claim 15, wherein embedding the claim-level features from the claim-level record to generate the claim-level vector comprises:
   for each claim-level feature, generating an N-dimensional claim-level vector; and
   concatenating the N-dimensional claim-level vectors to generate an M*N-dimensional claim-level vector representing the claim header, wherein M represents a number of claim-level features,
   wherein embedding the service line service line features from each of the service lines to generate a service line vector for each service line comprises:
   for each service line feature, generating an N-dimensional service line vector; and
   for each service line, generate an S*N-dimensional service line vector, wherein S is the number of service line features in each service line;
   generate an L-length sequence of S*N-dimensional service line vectors, wherein L is the number of service lines;
   wherein generating the predefined sized vector comprises:
   processing the M*N-dimensional claim-level vector and the L-length sequence of S*N-dimensional service line vectors through neural network layers to (a) identify the hierarchical relationships, and (b) reduce dimensionality to D by generating a D-dimensional claim header vector and L D-dimensional line vectors;
   pooling the L D-dimensional line vectors to generate a D-dimensional service-line vector; and
   concatenating the D-dimensional claim header vector with the D-dimensional service-line vector to generate the predefined sized vector as a D*2-dimensional vector.

* * * * *